United States Patent
Shoher et al.

(10) Patent No.: US 7,329,125 B2
(45) Date of Patent: Feb. 12, 2008

(54) METHOD FOR IMPROVING THE CEMENT RETENTION OF A DENTAL COPING TO A TOOTH STRUCTURE

(76) Inventors: Itzhak Shoher, 50 Shlomo Hamelech St., Tel Aviv (IL); Aharon Whiteman, L. Peretz St. 13, Petach Tikvak (IL)

( * ) Notice: Subject to any disclaimer, the term of this patent is extended or adjusted under 35 U.S.C. 154(b) by 213 days.

(21) Appl. No.: 10/860,169

(22) Filed: Jun. 4, 2004

(65) Prior Publication Data

US 2005/0272009 A1 Dec. 8, 2005

(51) Int. Cl.
*A61C 13/08* (2006.01)
(52) U.S. Cl. ............... 433/208; 433/218; 433/226; 428/323; 428/553; 75/255
(58) Field of Classification Search ........... 433/208, 433/207, 218, 223; 428/323, 553; 75/255
See application file for complete search history.

(56) References Cited

U.S. PATENT DOCUMENTS

| 4,433,958 | A | * | 2/1984 | Fellman et al. | 433/199.1 |
| 4,895,516 | A | * | 1/1990 | Hulten | 433/201.1 |
| 5,104,323 | A | * | 4/1992 | Mertens | 433/226 |
| 5,914,185 | A | * | 6/1999 | Shoher et al. | 428/323 |
| 6,083,005 | A | * | 7/2000 | Taub | 433/215 |
| 2003/0097906 | A1 | * | 5/2003 | Shoher et a. | 75/255 |
| 2003/0211444 | A1 | * | 11/2003 | Andrews | 433/172 |

* cited by examiner

*Primary Examiner*—Melba N. Bumgarner
*Assistant Examiner*—Jonathan Werner

(57) ABSTRACT

A method to increase the cement retention of a metal dental coping to the structure of a tooth in the preparation of a crown or bridge. The method includes forming a liquid composition of high and low fusing temperature metal particles with at least 50% of the high fusing metal particles having a thin cross-sectional average thickness of less than 5 microns and coating the interior surfaces of the metal coping with the liquid composition to form a thin coating of no greater than 20 microns before the coping is mounted on the tooth structure. The thin coating of liquid composition should then be heat treated at a temperature of between 750° C. and 1050° C. to permit the low-fusing temperature metal particles to fuse but not entirely melt. Following heat treatment a dental cement should be applied to the tooth structure or coping in a conventional manner. Thereafter, the coping is mounted on the tooth structure with the heat treated coating in contact with the dental cement to improve retention.

4 Claims, No Drawings

METHOD FOR IMPROVING THE CEMENT RETENTION OF A DENTAL COPING TO A TOOTH STRUCTURE

FIELD OF THE INVENTION

This invention relates to a method to increase cement retention between a metal dental coping and a tooth structure in the preparation of a crown or bridge dental restoration and to a composition to improve cementation of a metal coping to a tooth preparation.

BACKGROUND OF THE INVENTION

In crown and bridge prosthodontics, metal copings are conventionally used to provide the essential structural strength and rigidity necessary for a dental restoration to resist the forces of mastication. In a ceramic-to-metal dental restoration, the metal coping forms the understructure, over which is applied a fired-on coating of porcelain or an acrylic veneer.

The metal coping may be cast from an investment of a wax or plastic pattern of the tooth to be restored. An alternative procedure which does not require waxing, investing or casting and which currently has been gaining wide acceptance by many laboratory practitioners and dentists is to form the coping from a moldable dental material composition composed of a mixture of high and low fusing temperature metal particles, as disclosed, for example, in U.S. Pat. No. 5,593,305 and U.S. Pat. No. 5,914,185 respectively. The dental material as taught in these patents, the disclosure of which is herein incorporated by reference, forms a porous structure upon heat treatment having a high void volume of above at least 20%. Before heat treatment the dental material is molded into the shape of the tooth to be restored. The molded shape is self-supported and is converted upon heat treatment in a dental furnace into a porous structure essentially any without shrinkage.

In the completion of a dental restoration the metal coping is cemented to the tooth preparation. However, if the metal coping is not properly cemented or if the cement does not retain itself between the surface of the prepared tooth and the metal dental coping microleakage may occur which will lead to decay and infection. In fact, microleakage is a major factor in promoting tooth decay under a dental restoration and particularly at the cervical margin. Accordingly, retention of the cement between the surface of the prepared tooth and the metal dental coping is an important factor in the preparation of dental crown or bridge.

SUMMARY OF THE INVENTION

The method of the present invention comprises the steps of: coating the interior surfaces of a metal dental coping adapted to be mounted on a tooth preparation during the formation of a crown or bridge with a thin coating of no greater than 20 microns of a dental material formed of a wet composition comprising high and low temperature metal particles with less than 40% by volume high-fusing temperature metal particles and a non-viscous volatile binder; and firing the coated metal dental coping at a temperature between 750° C. and 1050° C. to permit the low-fusing temperature metal particles to fuse but not to entirely melt. The binder should preferably be a liquid in sufficient concentration such that the composition will have a void volume of between 20 to 80% and preferably between 40 to 60%. The particles should preferably all be below an average thickness of 50 microns with at least 50% of the high fusing particles having a thin cross-sectional average thickness of less than 5 microns and preferably less than 3 microns.

The present invention also relates to a composition for improving the retention of a metal dental crown to a tooth structure in the preparation of a crown or bridge dental restoration formed by the process of mixing particles of high and low fusing temperature metals or alloys thereof with a volatile non-viscous binder in liquid form wherein the low fusing temperature metal particles are equal to at least 60% by volume and applying the composition as a coating of no greater than 20 microns to the interior surfaces of the metal coping before mounting the coping on the tooth surface. The high fusing particles may be of any geometry including a spherical geometry although an irregular non-spherical platelet geometry is preferred with at least 50% of the particles having a thin cross-sectional average thickness of less than 5 microns and preferably less than 3 microns and an average length measured along the long axis thereof of less than 50 microns and preferably less than 20 microns. A borax or other known dental fluxing material may be included in the composition up to no more than 5% by weight.

DETAILED DESCRIPTION OF THE INVENTION

The composition used in the method of the present invention is formed by mixing low-fusing temperature metal particles, high-fusing temperature metal particles and a volatile non-viscous binder preferably in liquid form.

The binder may be any suitable vehicle which will permit the composition to be coated upon the interior surface of a metal coping. The binder should be a volatile non-viscous binder and preferably a liquid binder selected form the group consisting of water, alcohol, polyethylene glycol or a mixture thereof. The concentration of the binder is not critical and need only be sufficient to readily coat the composition upon the interior surfaces of a metal coping.

The particles of low-fusing temperature metal are composed of any biocompatible metal preferably of gold or silver or an alloy of gold or silver and are preferably of spherical geometry. Optimally gold is the sole or major constituent of the low-fusing temperature metal and although other metals may be included selected from the group of metals such as copper, zinc, aluminum, magnesium, gallium, indium, tin, or any of the platinum group metals and/or elements from the third or fourth groups of elements of the periodic table the total weight of the other metals should not exceed ten percent (10%) of the total weight of the low-fusing temperature metal component of the composition. The preference for gold as the major constituent of the low-fusing component is based on its known characteristics of workability, biocompatibility and non-oxidizing properties. It is important that the composition be non-oxidizing and if necessary a non-oxidizing dental flux can be added such as borax up to 5% by weight of the composition. The low-fusing metal particles should represent at least 60% of the dental composition by volume but preferably over 75% and optimally between 80% and 90% by volume. The low-fusing metal particles must, of course, have a melting temperature below that of the high-fusing metal particles.

The high-fusing temperature metal component should represent between 1 to 40% of the dental composition by volume and preferably between 1 to 25% and may be selected of a single metal or metal alloy, preferably of precious metals such as platinum and/or palladium, in any desired proportion relative to each other, from zero to one hundred percent, with or without other constituents such as gold, silver, copper, magnesium, aluminum, zinc, gallium, indium, and other metals or elements from the third, fourth, or fifth group of elements of the periodic table. Gold may be added to the high-fusing temperature metal component to increase the fusion affinity of the high-fusing temperature metal component to the low-fusing temperature metal component. The high fusing particles should have an irregular shape preferably of non-spherical platelet geometry with at least 50% of the particles having a thin cross-sectional average thickness of less than 5 microns and preferably less than 3 microns and an average length measured along the long axis thereof of less than 50 microns and preferably less than 20 microns.

In accordance with the preferred embodiment of the present invention, the low-fusing temperature metal particles are mixed with the high-fusing temperature metal particles and liquid binder to form a liquid or wet putty like material which can be coated by painting or brushing upon the interior surfaces of a metal dental coping.

After coating the composition to the interior surfaces of a metal dental coping, the coping is heat treated to cause the particles to fuse. The heat treatment may be done in a furnace at a temperature of between 750° C. and 1050° C. The heat treatment is preferably carried out at the glazing temperature of porcelain sufficient to permit the low-fusing temperature metal particles to fuse but not to entirely melt.

What we claim is:

1. A method to improve the retention of a gold based metal coping composed substantially or essentially of gold when cemented to a tooth structure in the preparation of a crown or bridge comprising the steps of: (1) forming a liquid composition comprising high and low fusing temperature metal particles with the high fusing temperature metal particles representing less than 25% by volume of the composition and with at least 50% of the high fusing temperature particles having a thin cross-sectional average thickness of less than 5 microns, (2) coating the interior surfaces of said gold based metal coping with said liquid composition to form a thin coating on the interior surface of the coping having a thickness of no greater than 20 microns, and (3) heat treating the coating of liquid composition at a temperature of between 750° C. and 1050° C. to permit the low-fusing temperature metal particles to fuse but not entirely melt so as to facilitate mounting the gold based metal coping on said tooth structure after applying a dental cement between the gold based metal coping and the tooth structure for improving the retention of the gold based metal coping to the tooth structure.

2. A method as defined in claim 1 wherein said low fusing temperature particles are composed of gold or silver or an alloy of gold or silver with gold or silver as the major constituent.

3. A method as defined in claim 2, wherein said composition includes a non-oxidizing dental flux of up to 5% by weight.

4. A method as defined in claim 2, wherein said liquid composition is selected from the group consisting of water, alcohol, polyethylene glycol or a mixture thereof.

* * * * *